(12) United States Patent
Goldenberg

(10) Patent No.: US 7,455,645 B2
(45) Date of Patent: *Nov. 25, 2008

(54) BONE MARROW BIOPSY NEEDLE

(76) Inventor: Alec S. Goldenberg, 157 E. 32nd St., Second Floor, New York, NY (US) 10016

( * ) Notice: Subject to any disclaimer, the term of this patent is extended or adjusted under 35 U.S.C. 154(b) by 0 days.

This patent is subject to a terminal disclaimer.

(21) Appl. No.: 11/965,354

(22) Filed: Dec. 27, 2007

(65) Prior Publication Data

US 2008/0154150 A1 Jun. 26, 2008

Related U.S. Application Data

(63) Continuation-in-part of application No. 11/416,451, filed on May 1, 2006, now Pat. No. 7,338,456.

(51) Int. Cl.
*A61B 10/00* (2006.01)
*A61B 17/32* (2006.01)

(52) U.S. Cl. .................. 600/564; 600/562; 600/567; 606/167; 606/170

(58) Field of Classification Search ................ 600/562, 600/564, 567, 568, 566; 606/167, 170
See application file for complete search history.

(56) References Cited

U.S. PATENT DOCUMENTS

| | | | |
|---|---|---|---|
| 3,605,721 A | 9/1971 | Hallac | |
| 4,262,676 A | 4/1981 | Jamshidi | |
| 5,074,311 A | 12/1991 | Hasson | |
| 5,522,398 A | 6/1996 | Goldenberg et al. | |
| 5,634,473 A | 6/1997 | Goldenberg et al. | |
| 6,015,391 A | 1/2000 | Rishton et al. | |
| 6,471,709 B1 | 10/2002 | Fawzi et al. | |
| 7,338,456 B2 * | 3/2008 | Goldenberg | 600/564 |
| 7,384,400 B2 * | 6/2008 | Goldenberg | 600/564 |
| 2007/0142744 A1 * | 6/2007 | Provencher | 600/562 |
| 2007/0219460 A1 * | 9/2007 | Goldenberg | 600/567 |

* cited by examiner

*Primary Examiner*—Max Hindenburg
*Assistant Examiner*—Emily M Lloyd
(74) *Attorney, Agent, or Firm*—Leason Ellis LLP

(57) ABSTRACT

A biopsy needle for removal of tissue from a patient includes an outer tube having a distal end and an inner tube disposed within the outer tube. The inner tube has a first section that includes a proximal end thereof, a second section that includes an actuatable snare, and a third section that includes a distal end thereof. The third section is coupled to the outer tube. The snare has a variable diameter that is controlled by rotation of the inner tube with respect to the outer tube in a prescribed direction resulting in the opening and closing, respectively, of the snare. The needle is configured such that the distal end of third section of the inner tube extends beyond the distal end of the outer tube such that the distal end of the inner tube represents a distal tip of the needle.

27 Claims, 5 Drawing Sheets

BONE MARROW BIOPSY NEEDLE

CROSS-REFERENCE TO RELATED APPLICATION

This application is a continuation-in-part of U.S. patent application Ser. No. 11/416,451, filed May 1, 2006, which is hereby incorporated by reference in its entirety.

TECHNICAL FIELD

This invention relates generally to a surgical instrument, known variously as a biopsy needle or biopsy cannula that is used to gather tissue, such as bone marrow, from living persons or animals for pathological study. More specifically, the invention relates to a biopsy needle having an improved structure for severing a tissue sample and/or retaining the tissue sample within the needle.

BACKGROUND

For various medical reasons, such as evaluating the histology and/or pathology of a tissue, it is often necessary for a physician to obtain a sample of a patient's body tissue. In particular, bone marrow is frequently retrieved to study its cellularity and potential infiltration with abnormal cells. The currently available procedures and instruments used for obtaining bone marrow biopsy samples, while not overly complex, almost universally result in excessive patient discomfort and often recover inadequate quantities of biopsy material which sometimes is distorted and/or difficult to interpret. In the standard bone marrow procurement protocol, using currently available instruments, (such as those disclosed in U.S. Pat. No. 4,262,676 to Khosrow Jamshidi), the patient is prepared with a suitable local anesthetic at the posterior superior iliac crest/spine. Then, a relatively narrow needle is inserted to obtain an aspirate of liquid bone marrow material to make slides for examination of cellular morphology and to evaluate the surface immunophenotype of the bone marrow cells with flow cytometry. This portion of the procedure, referred to as the bone marrow aspiration, is generally relatively less painful than the bone marrow biopsy procedure using a conventional biopsy needle. Using newer bone marrow biopsy needles which actively capture specimens, and minimize manipulation of the needle after insertion, the aspirate procedure appears to be more painful than the biopsy procedure.

After the aspirate is obtained, if necessary, a biopsy of the bone marrow is taken. A significantly wider bore needle having an inner diameter that will accommodate a suitable marrow sample is prepared with an inner stylet that extends beyond the distal end of the outer needle. The stylet's distal end may be cut at an angle, with the leading edge sufficiently sharp to pierce tissue and bone. With the stylet in place within the outer needle, the needle is pushed through the outer layers of skin and subcutaneous tissue until the needle tip reaches the surface of the cortical bone. The needle and stylet are then pushed into and through the cortical layer until the tip has penetrated into the bone marrow space.

The stylet is then removed from the proximal end of the needle, which opens up the core of the needle to accommodate entry of bone marrow material for collection and retrieval. The needle is then usually advanced another 1 to 2 centimeters at minimum with a slight twisting motion. Often, the distal end of the needle will also be provided with an angled cut and sharpened leading edge or scalloped serrations to facilitate cutting and coring the tissue. By providing a slight twisting motion as the needle is advanced, usually with no more than quarter or half turns, an appropriate sample is cored from the marrow tissue and enters the inner passage of the marrow needle.

At this point, the marrow biopsy sample is ready to be removed from the patient, although it is important that the biopsy remain within the needle as the needle is withdrawn to ensure recovery of the specimen. If the biopsy becomes dislodged and falls through the distal end of the biopsy needle, the specimen is irretrievably lost. The procedure is then unsuccessful and must be repeated from the beginning.

Various methods have been utilized by physicians to try to prevent the biopsy specimen from dislodging from the needle. For example, after the needle has entered the bone and fully cored a sample from the marrow, some physicians will pull the biopsy needle back a few millimeters and then advance it a few millimeters at a different angle than the first insertion. This theoretically will "cut" the biopsy piece at the tip of the needle. Other physicians attempt to dislodge or disrupt the connection between the specimen and the bone by making multiple complete clockwise and counterclockwise rotations of the biopsy needle while within the bone. Some physicians even hit the proximal end of the biopsy needle at its handle in an attempt to mechanically disrupt the connection between the specimen and the additional bone.

As can be plainly realized, these manipulations at the end of the procedure, attempts at ensuring that the specimen remains within the needle, can often produce substantial discomfort and anxiety to the patient. Sometimes when the bone marrow is very soft, as in patients with osteoporosis, almost all of these attempts are futile because the bone structure is so fragile. Conversely, sometimes when the bone marrow is very fibrotic, which occurs in patients with myelofibrotic diseases or in AIDS patients, it is difficult to dislodge the core biopsy, since the bone marrow itself is reinforced by the surrounding tissue. In those cases, the cored biopsy often remains attached to the bone and is not successfully recovered.

Other attempts at designing a more efficient and successful biopsy needle have met with little or no success, for various reasons, including the complexity of the devices. For example, U.S. Pat. No. 3,605,721 to Hallac, discloses a biopsy needle in which an inner tube has a weakened portion represented by strips extending between distal and proximal portions of the inner tube. The distal portion of the inner tube is adhered to an outer tube and will not rotate. Once a biopsy has entered the needle, the proximal portion of the inner tube is rotated, causing the strips to twist together and eventually break off. This twisting motion tends to twist the strips to the tube's center, thus hopefully keeping the biopsy piece proximal of the twisted and broken strips for later removal. This particular biopsy needle is only a disposable device, since the strips are broken or irreversibly warped by deformation during the twisting process. Another disadvantage is the lack of control over the twisting motions or the breakage of the strips. Essentially, the operator is left to twist the inner tube until resistance to that twisting is lost, indicating that the strips have severed. There is also no way of releasing the device's grip on tissue during the procedure, should any problems arise.

U.S. Pat. No. 5,074,311 to Hasson discloses a biopsy device that includes a pair of inner jaws that can be actuated within the outer needle to "bite off" any biopsy piece that has entered the needle. The disadvantages of this device include multiple small mechanical linkages and parts including pivot pins, which are extremely difficult and expensive to assemble and maintain, in addition to the greatly increased chance of mechanical failure resulting in failure to retrieve an adequate specimen.

U.S. Pat. No. 5,522,398, to Goldenberg et al., discloses a bone marrow biopsy needle; however, the patent teaches that an inner diameter B at the distal tip of the needle (as shown in FIG. 4 thereof) is substantially equal to an inner diameter C of the inner tube (as shown in FIG. 3C) so that there will be no ridge or lip within the instrument to impede tissue entering the inner lumen of the needle. However, observations over time of the performance of needles constructed in this manner indicates that such a relationship may impede specimen transit into and through the needle, and that a virtual obstruction phenomena may develop as a result of the above relationship between the two inner diameters. Compromise of specimen transit into the needle results in an inability of the specimen to move forward into the lumen of the needle. In addition, as the needle penetrates tissue, external pressures, especially those produced by dense bone, could deform or change the diameter at the needle tip (inner diameter B) or might transmit a force through the wall of the needle, marginally decreasing the diameter of the inner tube or snare (inner diameter C). These changes could dynamically alter the relationship between the inner diameters and cause a virtual obstruction, impeding specimen transit and making it difficult for the specimen to move forward into the needle.

SUMMARY

According to one embodiment, a biopsy needle for removal of tissue from a patient includes an outer tube having a distal end and an inner tube disposed within said the outer tube. The inner tube has a first section that includes a proximal end thereof, a second section that includes an actuatable snare, and a third section that includes a distal end thereof. The third section is coupled to the outer tube. The snare has a variable diameter that is controlled by rotation of the inner tube with respect to the outer tube in a prescribed direction resulting in the opening and closing, respectively, of the snare. The needle is configured such that the distal end of the third section of the inner tube extends beyond the distal end of the outer tube such that the distal end of the inner tube represents the distal tip of the needle. The snare coil has an inner diameter ($ID_{sc}$) and the third section at the distal tip has an inner diameter ($ID_{tip}$) and a ratio $(R)=(ID_{sc})/(ID_{tip})$ is greater than 1.

In another embodiment a biopsy needle for removal of tissue from a patient includes an outer tube having a distal end and an inner tube disposed within said outer tube. The inner tube has a first section that includes a proximal end thereof, a second section that includes an actuatable snare, and a third section that includes a distal end thereof. The third section is coupled to the outer tube. The snare has a variable diameter that is controlled by rotation of the inner tube with respect to the outer tube in a prescribed direction resulting in the opening and closing, respectively, of the snare. The needle is configured such that the distal end of the third section of the inner tube extends beyond the distal end of the outer tube such that the distal end of the inner tube represents the distal tip of the needle. The first section has an internal diameter ($ID_{pint}$) and the snare coil has an inner diameter ($ID_{sc}$) and a ratio $(R)=(ID_{pint})/(ID_{pint})$ is greater than 1.

BRIEF DESCRIPTION OF THE DRAWINGS

Other objects, advantages and embodiments than those described above will become apparent to those skilled in the art upon reading the following detailed description of the preferred embodiments in conjunction with a review of the appended drawings, in which.

DETAILED DESCRIPTION OF THE PREFERRED EMBODIMENTS

Figure 1:
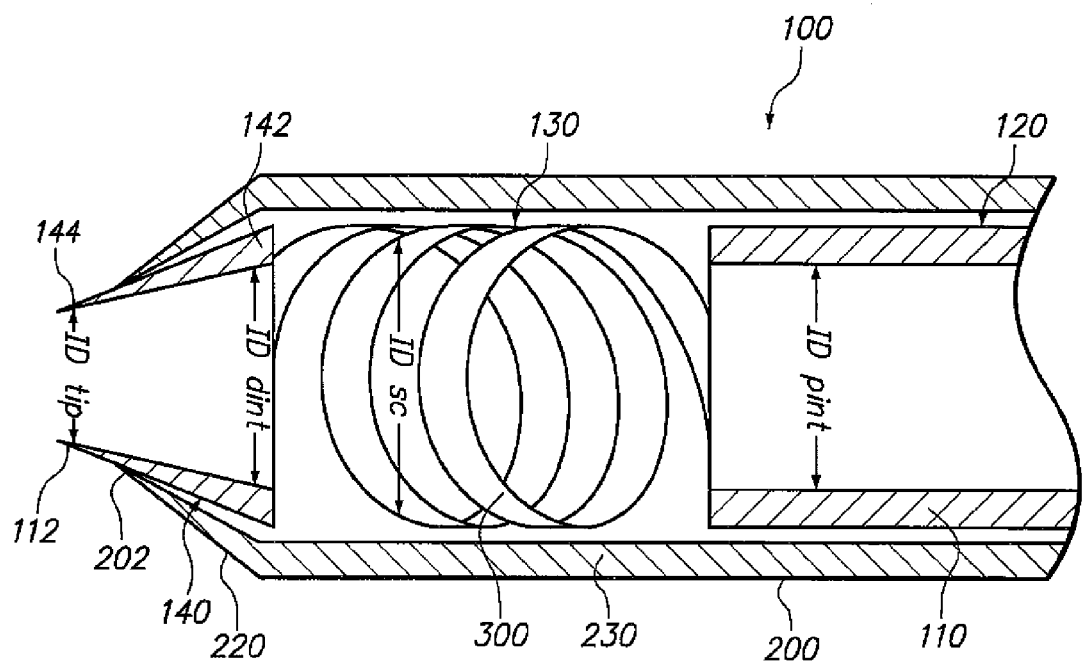
FIG. 1 is a cross-sectional view of a section of a biopsy needle in accordance with a first embodiment of the present invention.

Referring now to FIG. 1, a section of a biopsy needle 100 is illustrated according to one embodiment of the present invention. It will be appreciated that a number of components of the biopsy needle 100 are not shown for ease of illustration and to more clearly illustrate the features of the present invention. For example, a stylet that is typically used with the biopsy needle 100 and a handle assembly that is used to actuate the biopsy needle 100 are not shown in FIG. 1. However, the positioning of the stylet relative to the biopsy needle components and an exemplary handle assembly are illustrated in commonly owned U.S. Pat. Nos. 7,338,456 and 7,384,400, each of which is hereby incorporated by reference in its entirety.

The biopsy needle 100 is formed primarily of three components, namely, an inner tube or cannula 110, an outer tube or cannula 200 and a snare 300. It will be understood that the handle assembly (not shown) actuates the snare 300 within the outer cannula 200 without any movement of the outer cannula 200 relative to the patient (not shown) by allowing the inner tube to rotate relative to the outer tube.

The inner tube 110 has a first end (proximal end) (not shown) and an opposite second end (distal end) 112. The inner tube 110 is a hollow structure that can have a cylindrical shape, as shown, or it can have another shape, such as an oval, etc., so long as the outer tube 200 has a complementary shape to the inner tube 110 and the inner tube can rotate within the outer tube. The inner tube 110 thus has an outer surface that faces an inner surface of the outer tube 200 and an opposite inner surface.

It will be appreciated that the inner tube 110 can be thought of as having three distinct regions or sections, namely, a first section 120 that represents the most proximal section of the inner tube 110, a second section 130 that includes the snare 300, and a third section 140 that is more distal compared to the first and second sections 120, 130 and thus represents the most distal section of the inner tube 110 and the entire biopsy needle 100, as it extends distal to the outer tube. Each of these sections 120, 130, 140 has an associated internal diameter. In FIG. 1, the internal diameter of the first section 120 is designated ($ID_{pint}$).

The snare 300 has a construction that is the same as or similar to the snare structures illustrated in U.S. Pat. Nos. 7,338,456 and 7,384,400. In other words, the snare 300 can have a helical shape or other shapes that will allow the diameter of the snare to decrease or increase with inner tube rotation relative to the outer tube. It will be appreciated that the snare 300 represents a portion of the inner tube 110 that is offset and spaced from the distal end 112 of the inner tube 110. However, the snare 300 is located closer to the distal end 112 compared to its distance to the proximal end of the inner tube 110. The snare 300 has an internal diameter that is designated ($ID_{sc}$). However, it will be appreciated that the snare can have any number of different constructions so long as it is capable of winding down to capture a specimen and then later open for release of the specimen as a result of manipulation of one of the inner and outer tubes.

The third section 140 that represents the most distal portion of the inner tube 110 can be thought of as having two different portions or regions, namely, a first region 142 that is the more proximal region and is located adjacent or proximate the snare 300 and a second region 144 that is the more distal region and terminates in the distal end 112. The first region 142 can have a cylindrical or conical/cylindrical shape (conformation) and has an internal diameter that is designated ($ID_{dint}$) and refers to the internal diameter of the proximal portion of the third section, 140 of the inner tube 110. The second region 144 that is the most distal portion of the third section 140 and thus the most distal portion of the inner tube 110 has an internal diameter designated as ($ID_{tip}$) since, as illustrated in FIG. 1, this region is the most distal aspect of the entire biopsy needle 100 when the inner tube 110 and outer tube 200 are coupled to one another.

In the embodiment of FIG. 1, the third section 140 of the inner tube 110 has a conical shape (conformation) and does not include a cylindrical component and is coupled to the outer tube 200 at a location along its length. For example, the distal section, 140 of the inner tube 110 can be bonded or mechanically attached to the outer tube 200 (e.g., a heat weld or other connecting means can be formed between the two structures). Additional means for attaching the two together are disclosed in Applicant's two other patents incorporated by reference herein. Since only a conical portion of the third section 140 exists, the most proximal portion of the third section 140 has a greater internal diameter ($ID_{dint}$) than the inner diameter of the most distal portion of the third section 140, namely, ($ID_{tip}$) which forms the tip of the needle. In other words, ($ID_{dint}$)>($ID_{tip}$). The proximal portion (first region 142) of the third section 140, the snare/snare coil 300 and the first section 120 of the inner tube 110 all have the same inner diameter and therefore, ($ID_{dint}$)=($ID_{sc}$)=($ID_{pint}$).

Applicant has discovered, based on detailed observations regarding the comparative transit of specimens in snare coil type needles, that specimen transit is maximized and only occurs if a ratio (R)=($ID_{sc}$)/($ID_{tip}$) is greater than 1. In other words, the ratio of the snare coil internal diameter to the internal diameter of the distal tip formed by the inner tube is greater than one. One will appreciate that this relationship concerning the internal diameters is in contrast to the teachings of applicant's prior '398 patent and in addition applicant's other disclosed patents embodiments where the outer tube 200 defines the distal tip of the needle 100 as opposed to the inner tube 110 forming the distal tip of the needle as is the case in needle 100 of FIG. 1. Applicant has discovered that the above relationship and the construction illustrated in FIG. 1 optimizes the ability of the specimen to move forward into the needle and ultimately be captured within the snare 300 upon activation thereof. Also, the formation of the distal tip of the needle from the inner tube after sliding the inner tube into the outer tube during production improves the manufacturability of the device. As described above, in the '398 patent design, the distal tip inner diameter of the outer cannula was described as being substantially equal to the snare coil inner diameter, to eliminate the possibility that a smaller inner diameter of the snarecoil would result in the wall of the snarecoil 300 protruding into the lumen of the inner tube, causing the distal edge of the snarecoil wall to form an obstructing ridge. A specimen encountering a ridge-like obstruction prior to entry into the snare would not transit though the snarecoil 300 efficiently and could also be damaged as the specimen passed though the snare.

In accordance with the present invention, there is a direct correlation between needle performance and the ratio R which provides a valid descriptor of intraluminal specimen transit and needle performance. According to one embodiment R>1.00; according to a second embodiment, R≧1.15; according to a third embodiment, R≧1.20; according to a fourth embodiment, R≧1.25; according to a fifth embodiment, R≧1.30; and according to a sixth embodiment, R≧1.35. It will be appreciated that the above values are merely exemplary in nature and that other values are equally suitable so long as the ratio R eliminates the occurrence of the obstruction phenomena that makes it difficult for the specimen to move forward into the needle 100 or compromises specimen recovery at the conclusion of the procedure.

It will also be appreciated that since R represents a ratio, small differences in the values of the numerator and denominator can result in substantial practical and physical implications influencing specimen transit and needle performance. The applicant has therefore discovered that an R value of about 1.0 or less will produce a virtual obstruction, which is not desirable and will impede specimen transit through and into the lumen of the snare. This is in direct contrast to Applicant's previous patent where equivalence between the distal tip and the inner tube inner diameters was suggested, consistent with the concept of avoiding a ridge or lip between the distal tip and the inner tube that could impede tissue entering the instrument. In assembling the needle 100, prior to configuring the pointed geometry of the tip, the outer tube 200 can be disposed over the inner tube 110 and positioned relative to the inner tube as shown in FIG. 1. Subsequent reconfiguration of the tip by grinding, compression or other methods results in a configuration where the distal end 112 of the inner tube 110 protrudes beyond a distal end 202 of the outer tube 200. As shown in FIG. 1, the outer tube 200 includes two different sections, namely, a first section 230 that has a cylindrical shape and a second section 220 that can have a cylindrical shape or conical/cylindrical shape or a conical shape as in FIG. 1. The angles of the conical sections of the inner and outer tubes 110, 200 can be complementary to facilitate construction as shown in FIG. 1.

To activate the snare 300, the inner tube 110 is rotated relative to the outer tube 200 by manipulating the handle assembly to cause either the opening or closing of the snare 300. In FIG. 1, the attachment point between the inner tube 110 and the outer tube 200 is located at the conically shaped third section of the inner tube 140.

Figure 2:
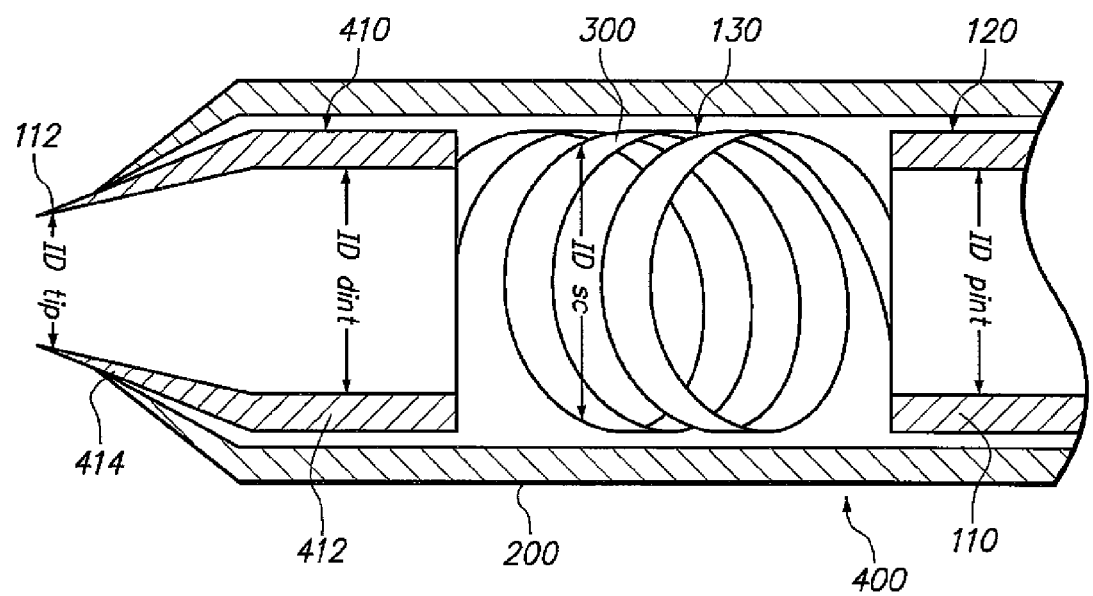
FIG. 2 is a cross-sectional view of a section of a biopsy needle in accordance with a second embodiment of the present invention.

Now turning to FIG. 2 in which a biopsy needle 400 according to a second embodiment is shown. Needle 400 is similar to needle 100 and therefore like elements are numbered alike.

In the embodiment of FIG. 2, a third section 410 of the inner tube is formed both by a cylindrical component (section) 412 and a distal conical component (section) 414. The attachment point between the inner tube 110 and the outer tube 200 is at this third section 410. For example, the third section 410 can be attached to the outer tube 200 by means of (1) attachment between the cylindrical section 412 and the outer tube 200, (2) attachment between the conical section 414 and the outer tube 200, or (3) attachment between both the cylindrical section 412 and conical section 414 and the outer tube 200.

The distal conical extension (section 414) of the inner tube 110 is the most distal portion of the needle 400 and its internal diameter ($ID_{tip}$) is the internal diameter of the inner tube 110 at its most distal end and consequently, the internal diameter ($ID_{tip}$) represents the internal diameter of the distal tip of the entire needle 400. Once again, specimen transit is acceptable and maximized when the internal diameter of the snare 300 ($ID_{sc}$) is greater than the internal diameter of the distal most portion of the entire needle 100 (($ID_{tip}$) defined by the distal most end of the third section 410 of the inner tube 110). In this configuration, as in the configuration of FIG. 1, ($ID_{dint}$)=($ID_{sc}$)=($ID_{pint}$), yet the snare 300 is displaced from the distal conical section 414 by the cylindrical section 412 of the third section 410.

Figure 3:
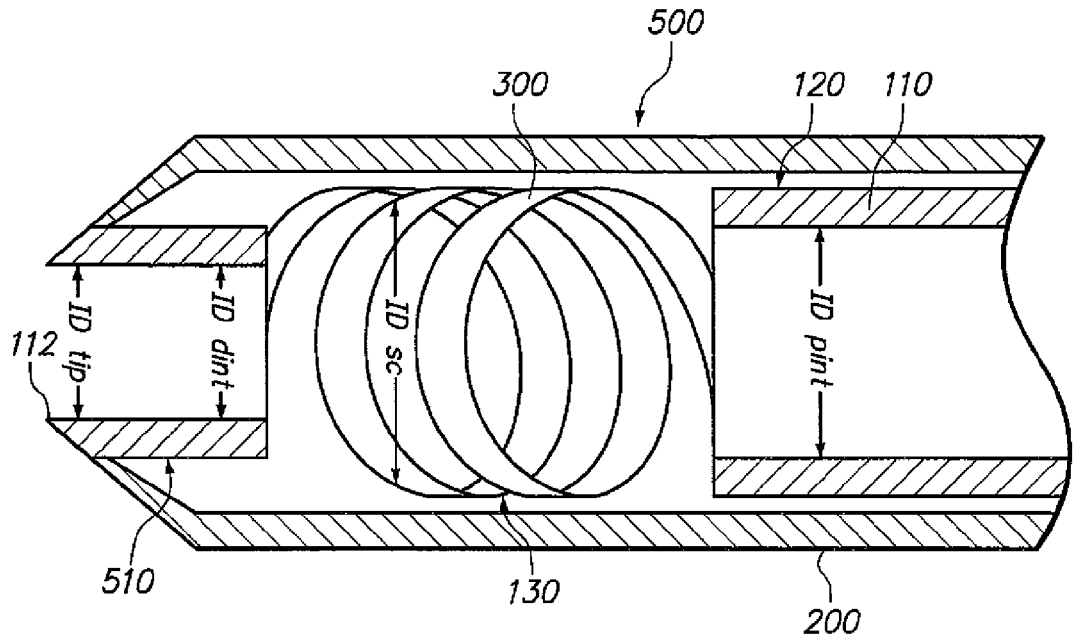
FIG. 3 is a cross-sectional view of a section of a biopsy needle in accordance with a third embodiment of the present invention.

Now referring to FIG. 3 in which a biopsy needle 500 according to a third embodiment is illustrated. Needle 500 is similar to the other needles and therefore, like elements are numbered alike. In this embodiment a third section 510 of the inner tube 110 has no distal conical component (section) and exists only as a cylindrical component (section). In this embodiment, the internal diameter of the third section 510 of the inner tube 110 is defined by ($ID_{dint}$)=($ID_{tip}$) or the inner diameter of the distal most portion of the third section 510 of the inner tube, ($ID_{dint}$) represents the inner diameter of the tip of the needle 500, ($ID_{tip}$). As with the other embodiments, specimen transit only occurs and is maximized when ($ID_{sc}$)/($ID_{tip}$)>1. In this configuration, the ratio of ($ID_{sc}$)/($ID_{dint}$), which is equal to the ratio ($ID_{sc}$)/($ID_{tip}$) is greater than 1, and the efficiency of specimen transit increases with shorter longitudinal lengths of the third section 510 of the inner tube 110. FIG. 3 also illustrates that the inner diameter of the more proximal portion (first section 120) of the inner tube 110 is the same as the inner diameter of the snare (snare coil) 300 and therefore, ($ID_{sc}$)=($ID_{pint}$).

Figure 4:
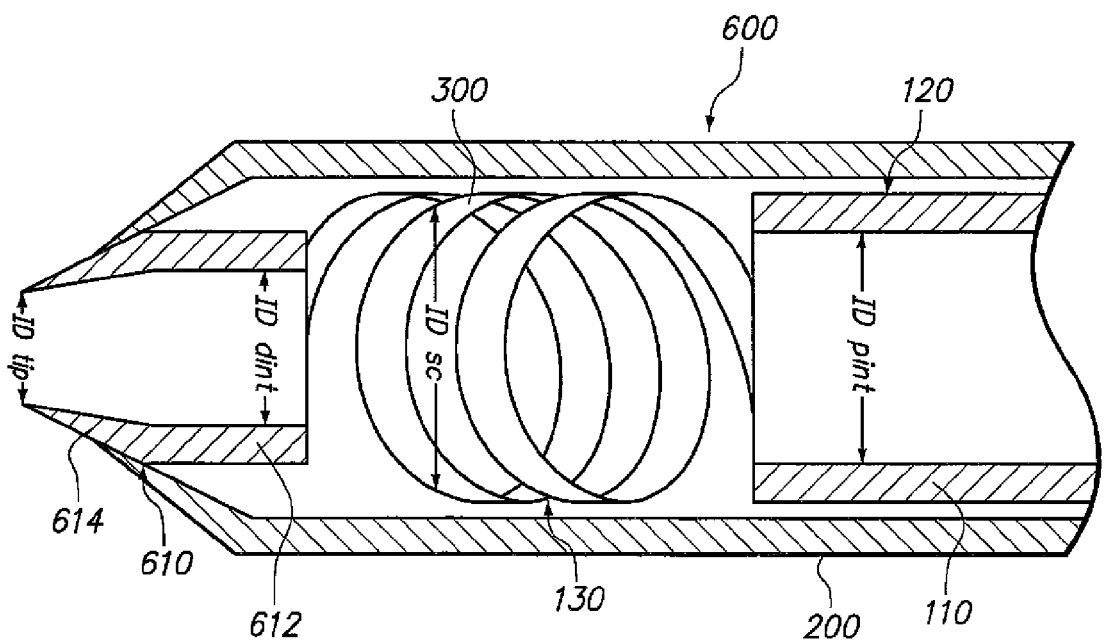
FIG. 4 is a cross-sectional view of a section of a biopsy needle in accordance with a fourth embodiment of the present invention.

Now referring to FIG. 4 in which a biopsy needle 600 according to another embodiment is illustrated. The biopsy needle 600 is similar to the needle 500 in FIG. 3 with the exception that a third section 610 of the needle 600 is not formed only by a cylindrical component (section) 612 but also has an additional distal conical element 614. Therefore, the inner diameter of the cylindrical component 612 of the third section 610 ($ID_{dint}$) is not equal to the inner diameter of the most distal portion (conical element 614) of the third section 610 which is the tip of the needle, i.e., the ($ID_{tip}$). In this embodiment, the more proximal portion (section 612) of the third section 610 has a greater diameter than the more distal portion of the distal component (section 614). In other words, ($ID_{dint}$)>($ID_{tip}$). As with the other embodiments, the ratio R=($ID_{sc}$)/($ID_{tip}$) should be greater than 1 for significant specimen transfer to occur to maximize recovery of the specimen. Moreover, the efficiency of the specimen transit will increase with shorter longitudinal lengths of the cylindrical component 612 of the third section 610 of the inner tube. Similar to the embodiment illustrated in FIG. 3, the internal diameter of the snare coil 300 and the internal diameter of the most proximal portion (first section 120) of the inner tube are the same resulting in ($ID_{sc}$)=($ID_{pint}$).

Figure 5:
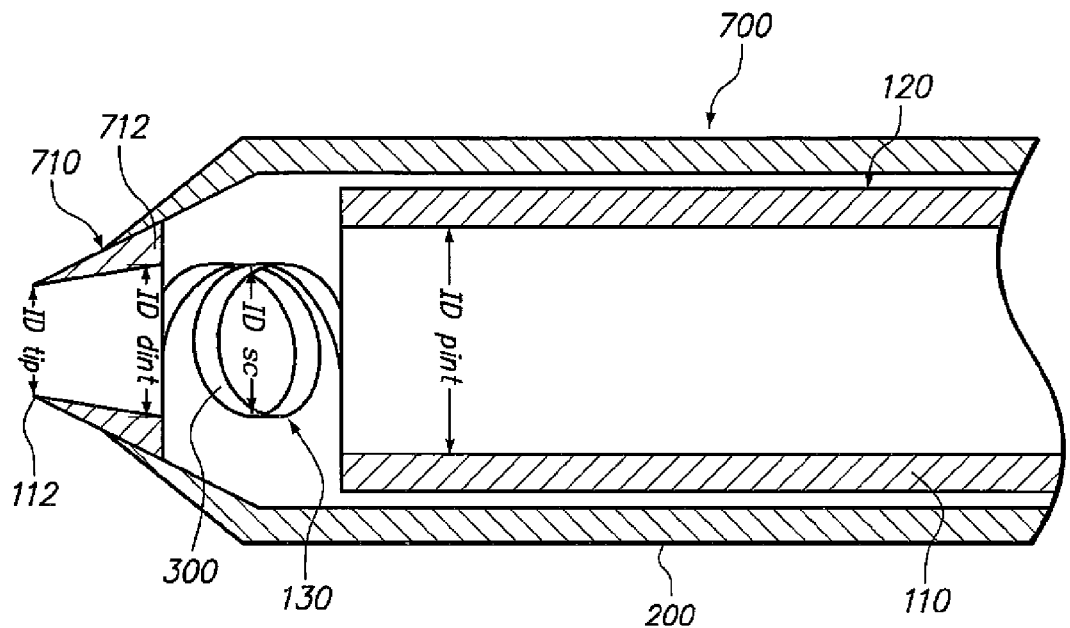
FIG. 5 is a cross-sectional view of a section of a biopsy needle in accordance with a fifth embodiment of the present invention.

Now referring to FIG. 5 in which a biopsy needle 700 according to another embodiment is illustrated. In this embodiment, the internal diameter of the most proximal portion (first section 120) of the inner tube 110 is greater than the internal diameter of the snare 300. A third section 710 of the needle 700 has a conical construction in which its most proximal inner diameter ($ID_{dint}$) is greater than the inner diameter at its most distal portion ($ID_{tip}$) which is the inner diameter of the tip of the needle 700. In this configuration, the inner diameter of a proximal portion 712 of the third section 710 is equal to the inner diameter of the snare 300 or ($ID_{dint}$)=($ID_{sc}$). In order to optimize performance characteristics and increase specimen transit, ($ID_{sc}$)/($ID_{tip}$)>1. However, the configuration offers the additional advantage for further increases in the diameter of the specimen as it transits into the needle 700, and therefore, improved specimen transit since ($ID_{pint}$)>($ID_{sc}$). It will be appreciated that needles having the type of construction shown in FIG. 5 will have improved specimen transit and specimen recovery if the longitudinal distance between the needle tip and the first section of the inner tube 120 is minimized, which can be achieved in part if the longitudinal distance of the snare 300 is minimized, thereby incorporating fewer full coil loops.

Figure 6:
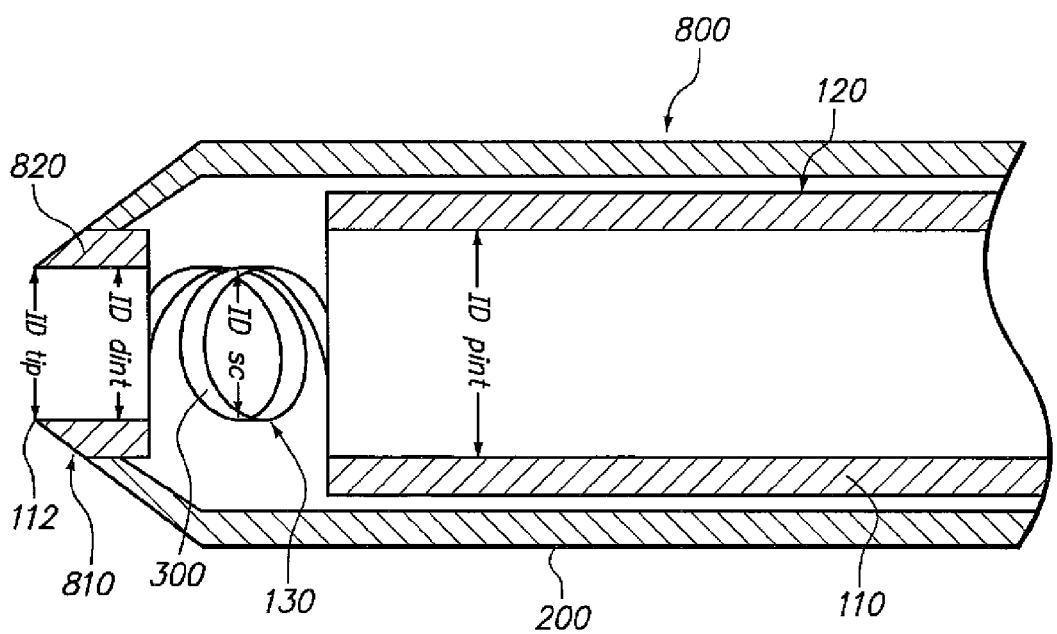
FIG. 6 is a cross-sectional view of a section of a biopsy needle in accordance with a sixth embodiment of the present invention.

Now referring to FIG. 6, a biopsy needle 800 according to another embodiment of the present invention is illustrated. The needle 800 includes a third section 810 that is formed only of a cylindrical element (section) 820 with no conical distal portion (section) being present. Therefore, the most proximal portion of the third section 810 has an internal diameter that is the same as the internal diameter of the most distal portion, which forms the distal tip, of the needle. In other words, ($ID_{dint}$)=($ID_{tip}$). Moreover, in this configuration, the internal diameter of the snare 300 is the same as the inner diameter both of the proximal and distal portion of the third section 810 of the inner tube or ($ID_{dint}$)=($ID_{tip}$)=($ID_{sc}$). This configuration consequently does not conform to the convention that ($ID_{sc}$)/($ID_{tip}$)>1, but instead, specifies that the ratio ($ID_{pint}$)/($ID_{sc}$) is greater than 1.

In other words, the step up of diameters occurs between the snare 300 and the proximal portion of the inner tube 110. Therefore, this configuration will only serve the purpose of increasing and facilitating specimen transit if the longitudinal displacement of the junction between the proximal portion of the snare 300 and the distal portion of the first section 120 of the inner tube 110 is minimally displaced from the tip 112 of the needle 800.

It will therefore be understood that the R-factor requirement of the present invention offers improved specimen transit since it predicts for smooth, non-obstructed travel of the specimen into the distal tip and then into and through the snare and into the proximal portion of the inner tube. In other words, by having a reduced diameter section followed by a larger diameter snare located within the interior of the outer cannula and spaced from the distal tip thereof, the specimen travels from a reduced diameter section (distal tip section) into a greater diameter section (compartment), namely, the interior of the open snare, without encountering an obstruction that can break apart the specimen or impede the travel of the specimen into the snare as in the prior art devices. This design results in improved capture of representative undistorted pathologic specimens due to improved specimen transit into and through the distal tip and then into and through the snare.

It will also be appreciated that the snare 300 shown in FIGS. 1-6 can be replaced by a snare configuration that is formed of a plurality of deformable members that are configured to deform inward upon rotation of the inner tube 110 relative to the outer tube 200 so as to effectively reduce the diameter of the inner tube 110 within a zone of deformation for obtaining a tissue sample within the inner tube 110. In particular and with reference to FIGS. 7A-7E, the snare 300 of FIGS. 1-6 can be substituted with a snare 300'. FIGS. 7A-E illustrate different embodiments where the snare 300' includes two (FIGS. 7A-C), six (FIG. 7D) or seven (FIG. 7E) deformable members. The figures, however, are only exemplary and snare configurations with three, four, or five or more then seven deformable members are possible. Also the representation of the snares as coil like structures is only exemplary and other configurations of deformable elements such as curvilinear strands having their long axis orientated along the longitudinal axis of the needle are possible.

Figure 7A:
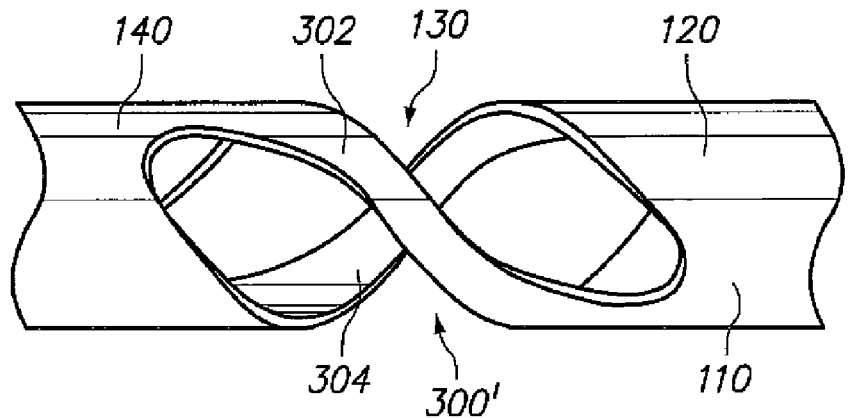
FIG. 7A shows an enlarged view of an exemplary snare having two deformable members.
Figure 7B:
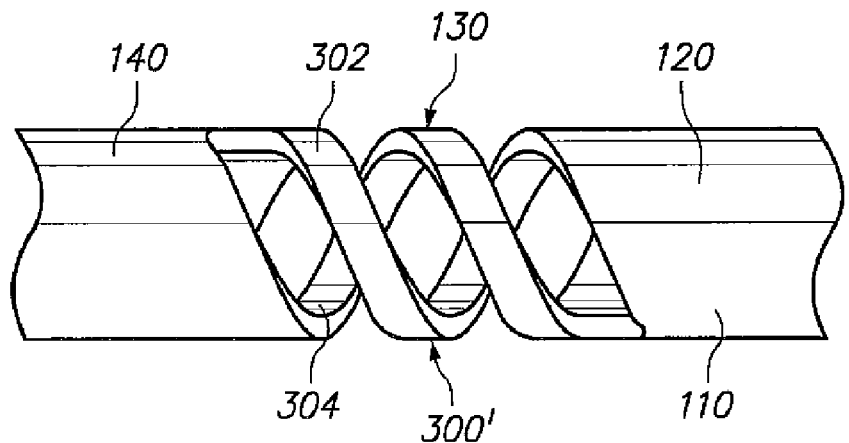
FIG. 7B shows an enlarged view of an exemplary snare with two deformable members, each forming a single coil.
Figure 7C:
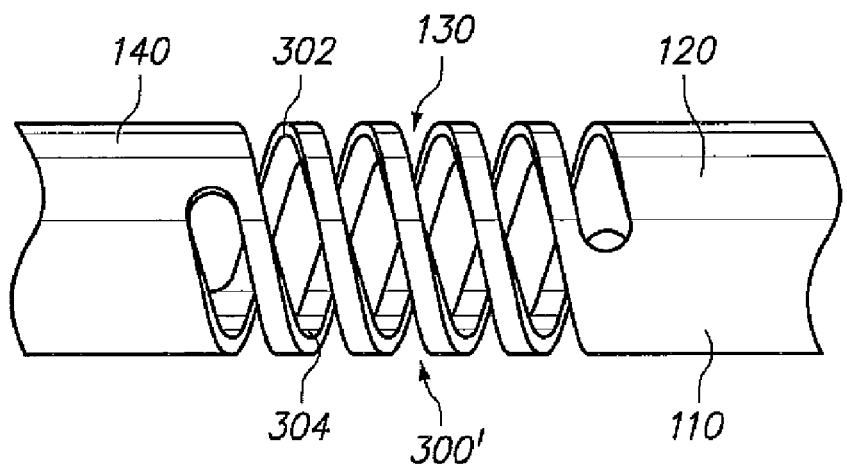
FIG. 7C shows an enlarged view of an exemplary snare with two deformable members, each forming a double coil.
Figure 7D:
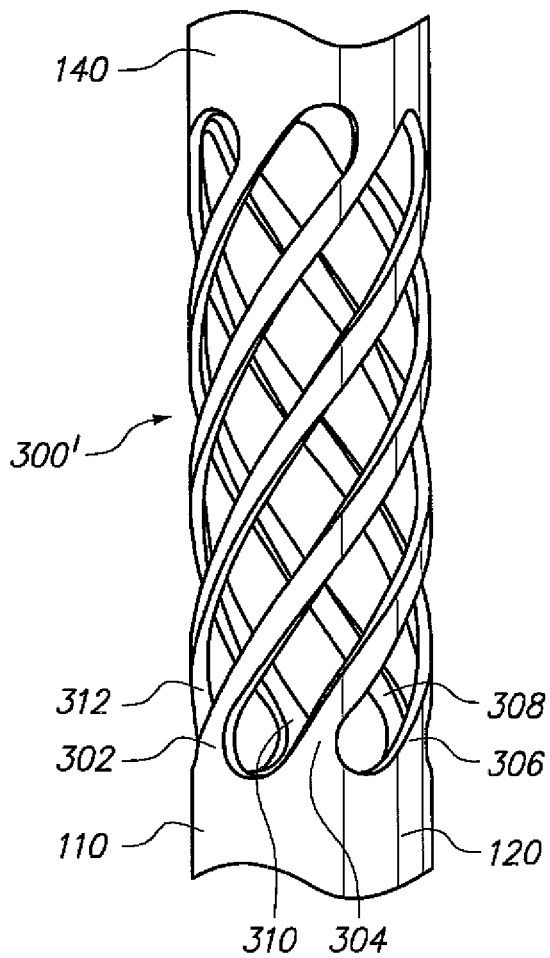
FIG. 7D shows an enlarged view of an exemplary snare with six deformable members.
Figure 7E:
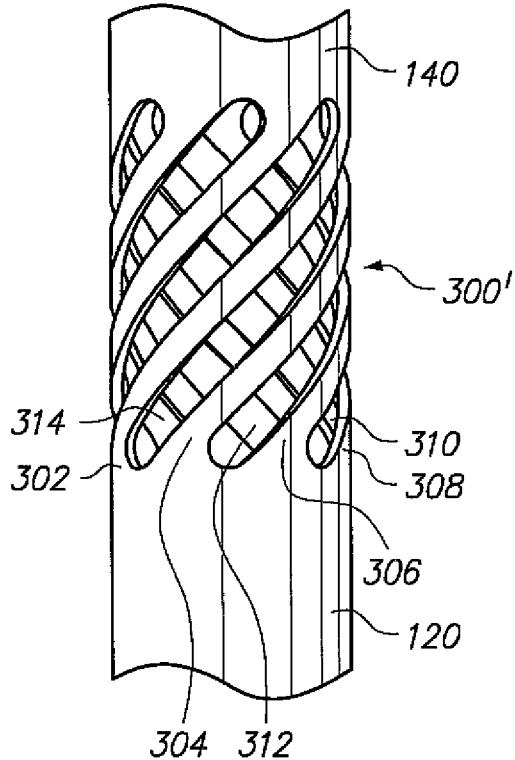
FIG. 7E shows an enlarged view of an exemplary snare with seven deformable members, each forming a single coil.

For example, FIG. 7A shows an enlarged view of snare 300' formed of two deformable members 302, 304. FIG. 7B shows an enlarged view of snare 300' formed of two deformable members 302, 304, each forming a single coil. FIG. 7C shows an enlarged view of an exemplary snare 300' with two deformable members, each forming a coil with two full 360 degree turns. FIG. 7D shows an enlarged view of snare 300' formed of six deformable members 302, 304, 306, 308, 310, 312. FIG. 7E shows an enlarged view of snare 300' formed of seven deformable members 302, 304, 306, 308, 310, 312, 314. It will be understood that other snare constructions can exist with more deformable members so long as once the inner tube and outer tube are rotated relative to one another, the snare is actuated.

Figure 8:
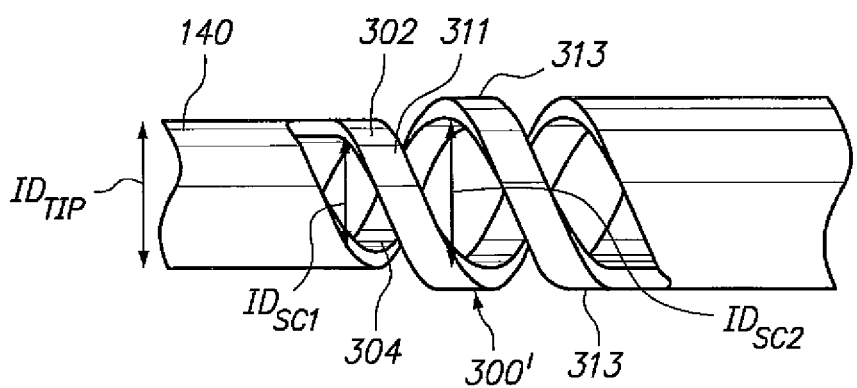
FIG. 8 shows an enlarged view of an exemplary snare with two deformable members, each forming a single coil, and the snare has a non-uniform inner diameter.

In another embodiment shown in FIG. 8, the inner diameter of the snare 300' can be non-uniform. In particular, a more distal portion or end 311 of the snare 300' has an inner diameter that is different from the inner diameter of a more proximal portion or end 313. For example, the distal portion 311 of the snare 300' has an inner diameter $(ID_{sc1})$ that is less than an inner diameter $(ID_{sc2})$ of the proximal portion 313 or $(ID_{sc2})/(ID_{sc1}) > 1$. This arrangement results if n the improved specimen transit and capture as discussed above. In addition, in one embodiment, $(ID_{sc1})/(ID_{tip})$ is greater than 1 and in an additional embodiment $(ID_{sc2})/(ID_{tip})$ is greater than 1. Alternatively, $(ID_{sc1})$ can be equal to $(ID_{tip})$ so long as $(ID_{sc2})$ is greater than $(ID_{tip})$. Thus, the R factor relationship can be incorporated into the snare 300' itself to permit improved specimen transit as described herein.

In one embodiment, the coils of the snare 300' can have an increasing diameter from the distal portion 311 to the proximal portion 313. The R factor relationship can thus be formed between adjacent coils of the snare 300'.

In addition, it will also be appreciated that any one of the snare 300' configurations can be used in one of the needle constructions shown in the '451 or '333 applications where the distal tip (distal end) of the needle is defined by the distal end of the outer tube.

While the embodiments shown and described above are fully capable of achieving the objects and advantages of the present invention, it is to be understood that these embodiments are shown and described solely for the purposes of illustration and not for limitation.

What is claimed is:

1. A biopsy needle for removal of tissue from a patient comprising: an outer tube having a distal end; an inner tube disposed within said outer tube, the inner tube having a first section that includes a proximal end thereof, a second section that includes an actuatable snare, and a third section that includes a distal end thereof, the third section being coupled to the outer tube, wherein the snare has a variable diameter that is controlled by rotation of the inner tube with respect to the outer tube in a prescribed direction resulting in the opening and closing, respectively, of the snare, the distal end of the third section of the inner tube extending beyond the distal end of the outer tube such that the distal end of the inner tube represents a distal tip of the needle, wherein the snare coil has an inner diameter $(ID_{sc})$ and the third section at the distal tip has an liner diameter $(ID_{tip})$ and a ratio $(R)=(ID_{sc})/(ID_{tip})$ is greater than 1.

2. The biopsy needle of claim 1, wherein the third section has a conical shape.

3. The biopsy needle of claim 1, wherein the first section of the inner tube has an inner diameter $(ID_{pint})$ and the third section of the inner tube has a proximal portion adjacent the snare that has an inner diameter $(ID_{dint})$ such that $(ID_{sc})=(ID_{dint})=(ID_{pint})$.

4. The biopsy needle of claim 1, wherein the outer tube has a distal end section terminating in the distal end, the distal end section having a conical shape, with the distal end of the inner tube protruding beyond the distal end section.

5. The biopsy needle of claim 1, wherein the third section has a cylindrical proximal portion and a conical distal portion that terminates in the distal end of the inner tube.

6. The biopsy needle of claim 5, wherein the cylindrical proximal portion has an inner diameter $(ID_{dint})$ that is greater than the inner diameter $(ID_{tip})$ that is defined at the distal end of the conical distal portion.

7. The biopsy needle of claim 6, wherein $(ID_{dint})=(ID_{sc})=(ID_{pint})$, where $(ID_{pint})$ is an inner diameter of the first section of the inner tube.

8. The biopsy needle of claim 5, wherein the cylindrical proximal portion is attached to the outer tube.

9. The biopsy needle of claim 5, wherein the conical distal portion is attached to the outer tube.

10. The biopsy needle of claim 1, wherein the third section has a cylindrical shape of uniform inner diameter with the distal end being a free end of the cylindrically shaped third section.

11. The biopsy needle of claim 10, wherein the first section has an inner diameter $(ID_{pint})$ that is equal to $(ID_{sc})$ and thus is greater than the inner diameter of the third section, including $(ID_{tip})$.

12. The biopsy needle of claim 1, wherein the third section has a cylindrical proximal portion and a conical distal portion that terminates in the distal end of the inner tube, wherein the cylindrical proximal portion has an inner diameter $(ID_{dint})$ that is greater than the inner diameter $(ID_{tip})$ that is defined at the distal end of the conical distal portion and $(ID_{dint})$ is less than $(ID_{sc})$, and $(ID_{dint})$ is also less than an inner diameter $(ID_{pint})$ of the first section.

13. The biopsy needle of claim 1, wherein the third section has a conical shape that has an inner diameter $(ID_{dint})$ at its most proximal end adjacent the snare, with the inner diameter $(ID_{pint})$ being defined at the distal end of the conical shaped third section.

14. The biopsy needle of claim 13, wherein ($ID_{dint}$) is greater than ($ID_{tip}$) and ($ID_{pint}$) is greater than ($ID_{sc}$), where ($ID_{pint}$) is an inner diameter of the first section of the inner tube.

15. The biopsy needle of claim 14, wherein ($ID_{dint}$)=($ID_{sc}$).

16. The biopsy needle of claim 1, wherein R is greater than 1.15.

17. The biopsy needle of claim 1, wherein R is greater than 1.20.

18. The biopsy needle of claim 1, wherein R is greater than 1.25.

19. The biopsy needle of claim 1, wherein R is greater than 1.30.

20. The biopsy needle of claim 1, wherein R is greater than 1.35.

21. The biopsy needle of claim 1, wherein the third section includes a distal end section that terminates in the distal end and has a beveled outer surface, the outer tube having a distal end section that terminates in the distal end and has a beveled outer surface that interfaces with and smoothly transitions to the beveled outer surface of the inner tube to form a tapered distal end section of the needle defined.

22. The biopsy needle of claim 1, wherein the snare comprises a plurality of deformable members configured to deform inward upon rotation of the inner tube relative to the outer tube so as to effectively reduce the diameter of the inner tube within a zone of deformation for obtaining a tissue sample within the inner tube.

23. The biopsy needle of claim 22, wherein the snare has a non-uniform inner diameter and the inner diameter ($ID_{sc}$) is defined as the inner diameter of at least one coil of the snare coil.

24. The biopsy needle of claim 23, wherein a distal-most portion of the snare has an inner diameter ($ID_{sc1}$) that is less than an inner diameter ($ID_{sc2}$) of a more proximal portion of the snare, and wherein the ratio ($ID_{sc2}$)/($ID_{sc1}$) is greater than one.

25. A biopsy needle for removal of tissue from a patient comprising: an outer tube having a distal end; an inner tube disposed within said outer tube, the inner tube having a first section that includes a proximal end thereof, a second section that includes an actuatable snare, and a third section that includes a distal end thereof, the third section being coupled to the outer tube, wherein the snare has a variable diameter that is controlled by rotation of the inner tube with respect to the outer tube in a prescribed direction resulting in the opening and closing, respectively, of the snare, the distal end of the third section of the inner tube extending beyond the distal end of the outer tube such that the distal end of the inner tube represents a distal tip of the needle, wherein the first section has an internal diameter ($ID_{pint}$) and the snare coil has an inner diameter ($ID_{sc}$) and a ratio (R)=($ID_{pint}$) is greater than 1.

26. The biopsy needle of claim 25, wherein the third section has a cylindrical shape of uniform inner diameter, including inner diameter ($ID_{tip}$) at the distal end thereof and ($ID_{tip}$)=($ID_{sc}$).

27. The biopsy needle of claim 25, wherein the first section has a cylindrical shape.

* * * * *